United States Patent
Seo et al.

(10) Patent No.: US 9,328,358 B2
(45) Date of Patent: May 3, 2016

(54) METHOD OF PRODUCING 2, 3-BUTANEDIOL USING RECOMBINANT YEAST

(71) Applicant: SNU R&DB Foundation, Seoul (KR)

(72) Inventors: Jin Ho Seo, Seoul (KR); Soo Jung Kim, Seoul (KR); Seung Oh Seo, Chungcheongbuk-Do (KR)

(73) Assignee: SNU R&DB Foundation, Seoul (KR)

( * ) Notice: Subject to any disclaimer, the term of this patent is extended or adjusted under 35 U.S.C. 154(b) by 0 days.

(21) Appl. No.: 14/293,711

(22) Filed: Jun. 2, 2014

(65) Prior Publication Data

US 2015/0167027 A1 Jun. 18, 2015

(30) Foreign Application Priority Data

Dec. 12, 2013 (KR) .......................... 10-2013-0154359

(51) Int. Cl.
 *C12P 7/18* (2006.01)
(52) U.S. Cl.
 CPC ........... *C12P 7/18* (2013.01); *C12Y 202/01006* (2013.01); *C12Y 401/01005* (2013.01); *C12Y 101/0101* (2013.01); *C12Y 101/01004* (2013.01); *C12Y 101/01307* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 2004/0142456 A1* | 7/2004 | Jeffries et al. | 435/254.21 |
| 2009/0305363 A1* | 12/2009 | Anthony et al. | 435/115 |
| 2011/0039327 A1* | 2/2011 | Winkler et al. | 435/254.21 |

FOREIGN PATENT DOCUMENTS

| | | |
|---|---|---|
| KR | 10-2012-0107021 A | 9/2012 |
| KR | 10-2012-0128776 A | 11/2012 |

* cited by examiner

*Primary Examiner* — Nashaat Nashed
(74) *Attorney, Agent, or Firm* — Mintz Levin Cohn Ferris Glovsky and Popeo, P.C.; Kongsik Kim; Elaine V. Morlock

(57) ABSTRACT

Disclosed is a method of producing 2,3-butanediol using a recombinant yeast having a 2,3-butanediol biosynthesis pathway controlled in a metabolic engineering manner. The method enables production of 2,3-butanediol at high production efficiency from glucose or xylose using a recombinant yeast wherein enzymatic activity of pyruvate decarboxylase is inhibited and exotic genes associated with 2,3-butanediol biosynthesis are introduced.

12 Claims, 14 Drawing Sheets

METHOD OF PRODUCING 2, 3-BUTANEDIOL USING RECOMBINANT YEAST

CROSS-REFERENCE TO RELATED APPLICATIONS

This application claims priority to Korean Application No. 10-2013-0154359 filed Dec. 12, 2013, which is incorporated herein by reference.

INCORPORATION BY REFERENCE

The contents of the text file named "48092-517001US_ST25.TXT," which was created on Aug. 25, 2015 and is 2.95 KB in size, are hereby incorporated by reference in their entirety.

TECHNICAL FIELD

The present invention relates to a method of producing 2,3-butanediol in a biological manner, and more specifically, to a method of producing 2,3-butanediol using recombinant yeasts having a 2,3-butanediol biosynthesis pathway controlled in a metabolic engineering manner. More specifically, the present invention relates to a method of producing 2,3-butanediol from glucose or xylose using recombinant yeasts wherein enzymatic activity of pyruvate decarboxylase is inhibited and exotic genes associated with 2,3-butanediol biosynthesis are introduced.

RELATED ART

Bioplatform compounds are produced by biological or chemical transformation based on biomass-derived materials and are used for synthesis of polymers, novel materials and the like.

Among bioplatform compounds, 2,3-butanediol is a compound used for synthesizing solvents, antifreeze liquids and plasticizers, which may be converted into butadiene used for production of synthetic rubbers, methyl ethyl ketone used as a fuel additive, and acetoin and diacetyl used as food additives and thus attracts much attention.

2,3-butanediol is generally produced by a biological method using microorganism fermentation, which requires development of novel strains using metabolic engineering techniques and optimization of fermentation processes. In addition, development of strains that can use fibrous biomass, which is cheaper than crop-based biomass, as a substrate is considerably essential consideration for price competitive production of 2,3-butanediol.

Conventionally used typical 2,3-butanediol-producing strains include *Klebsiella oxytoca, Klebsiella pneumoniae, Aerobacter aerogenes* and the like. These strains are known to be capable of producing 2,3-butanediol at a high yield and a high production efficiency. However, most of these strains are classified into pathogenic microorganisms, causing restriction in terms of safety and industrialization. Accordingly, there is a need for selection and development of strains capable of producing 2,3-butanediol at a high efficiency using non-pathogenic microorganisms.

An alternative to this may be development of production of 2,3-butanediol using yeasts known as GRAS (generally recognized as safe) microorganisms. However, wild yeasts have the following limitations to use as 2,3-butanediol-producing strains.

First, yeast has a 2,3-butanediol biosynthesis pathway more inefficient than 2,3-butanediol-producing bacteria.

Second, yeast uses pyruvate as a main precursor of 2,3-butanediol for production of ethanol, thus providing a considerably lower 2,3-butanediol yield than 2,3-butanediol-producing bacteria.

Finally, yeast is incapable of metabolizing xylose as a major carbon source in lignocellulosic biomass, thus making economical production of 2,3-butanediol using lignocellulosic biomass as a substrate difficult.

SUMMARY

Therefore, the present invention has been made in view of the above problems, and it is one object of the present invention to develop and provide a method of producing 2,3-butanediol at high production efficiency from glucose or xylose using *Saccharomyces cerevisiae* known as a yeast.

In accordance with the present invention, the above and other objects can be accomplished by the provision of recombinant *Saccharomyces cerevisiae* transformed such that functions of pyruvate decarboxylase is lost, and acetolactate synthase, acetolactate decarboxylase and butanediol dehydrogenase are expressed.

BRIEF DESCRIPTION OF THE DRAWINGS

The above and other objects, features and other advantages of the present invention will be more clearly understood from the following detailed description taken in conjunction with the accompanying drawings, in which.

Figure 10:
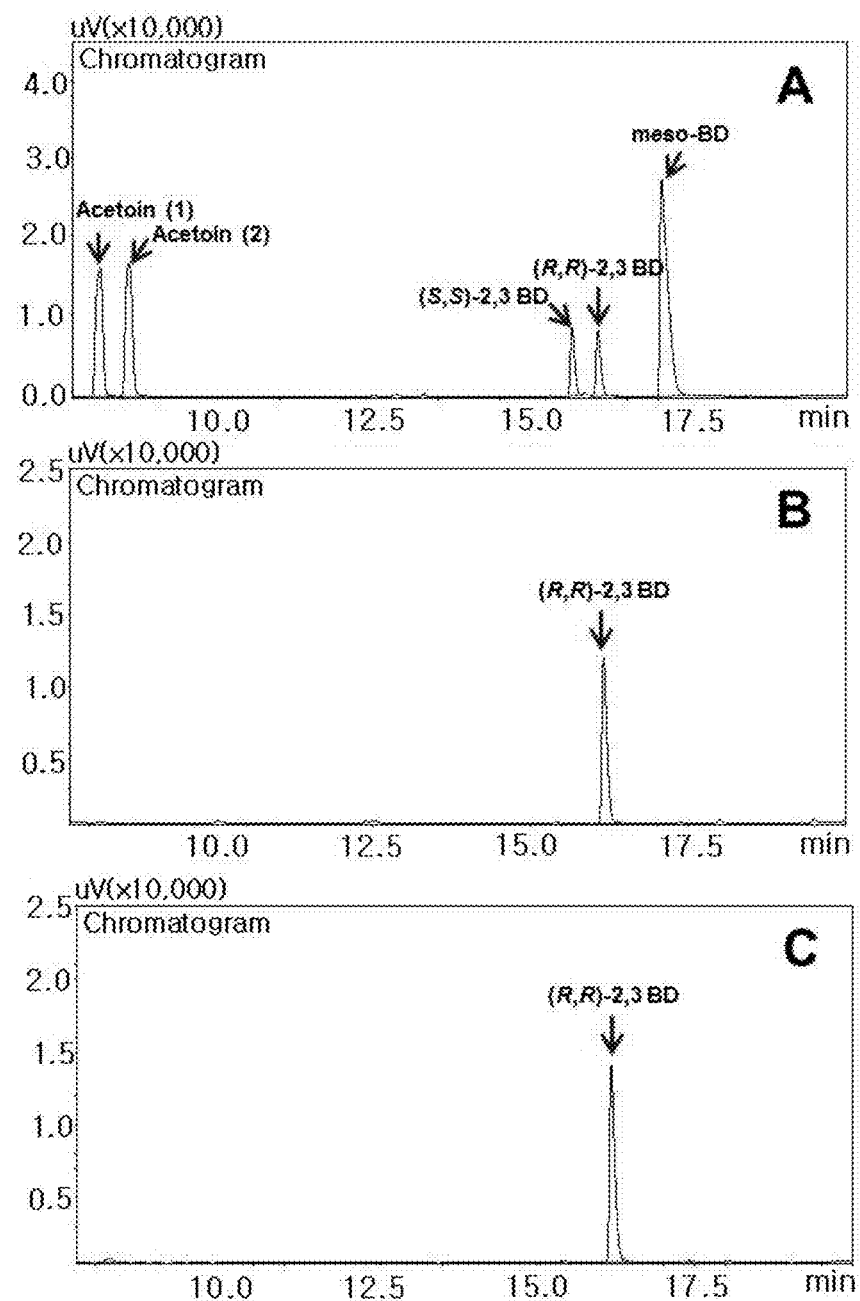
Figure 11:
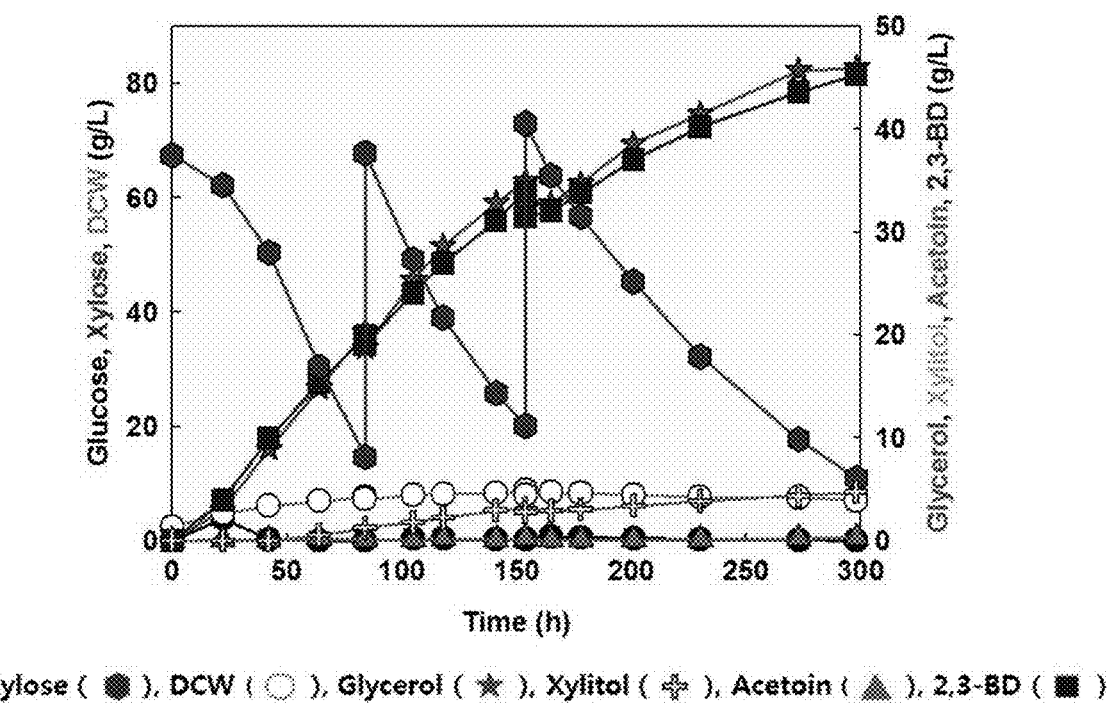
Figure 12:
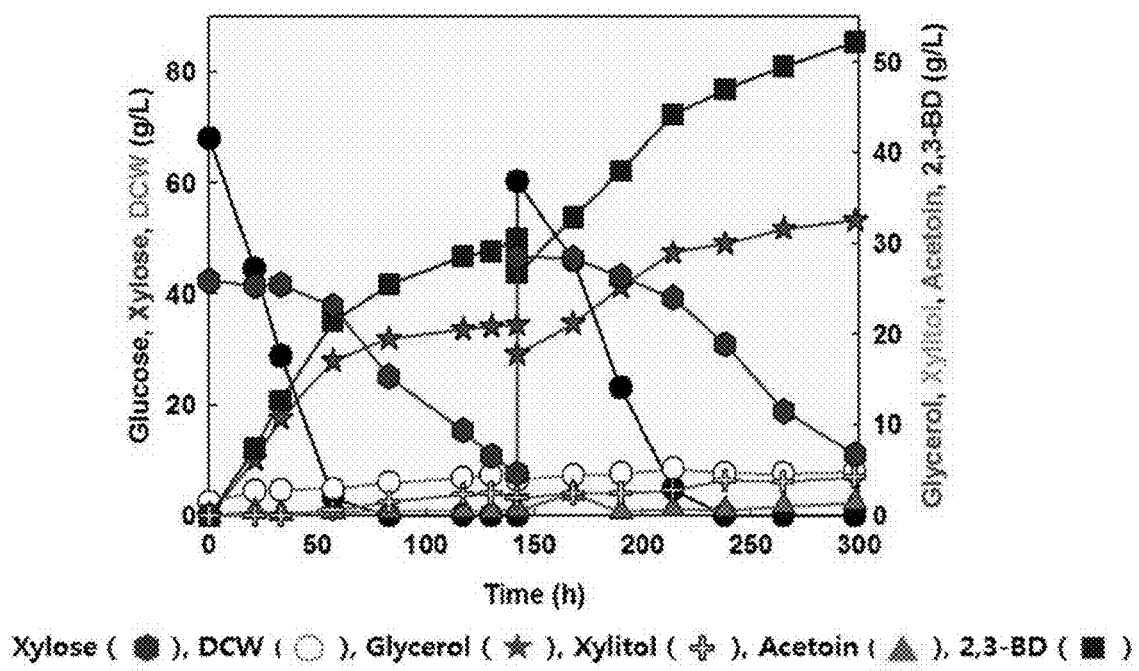

YP medium containing 8% xylose, (B): YP medium containing 2% glucose and 8% xylose;

FIG. 10 shows results of GC analysis on stereoisomers of 2,3-butanediol produced by BD4X strains. (A) acetoin and 2,3-butanediol standards, (B) 2,3-butanediol stereoisomers produced by BD4X strain through metabolization of glucose, (C) 2,3-butanediol stereoisomers produced by BD4X strains through metabolization of xylose;

FIG. 11 shows results of xylose fed-batch culture of BD4X strains with a limited glucose supply under microaerobic conditions; and FIG. 12 shows results of glucose and xylose fed-batch culture of BD4X strains under microaerobic conditions.

Figure 13:
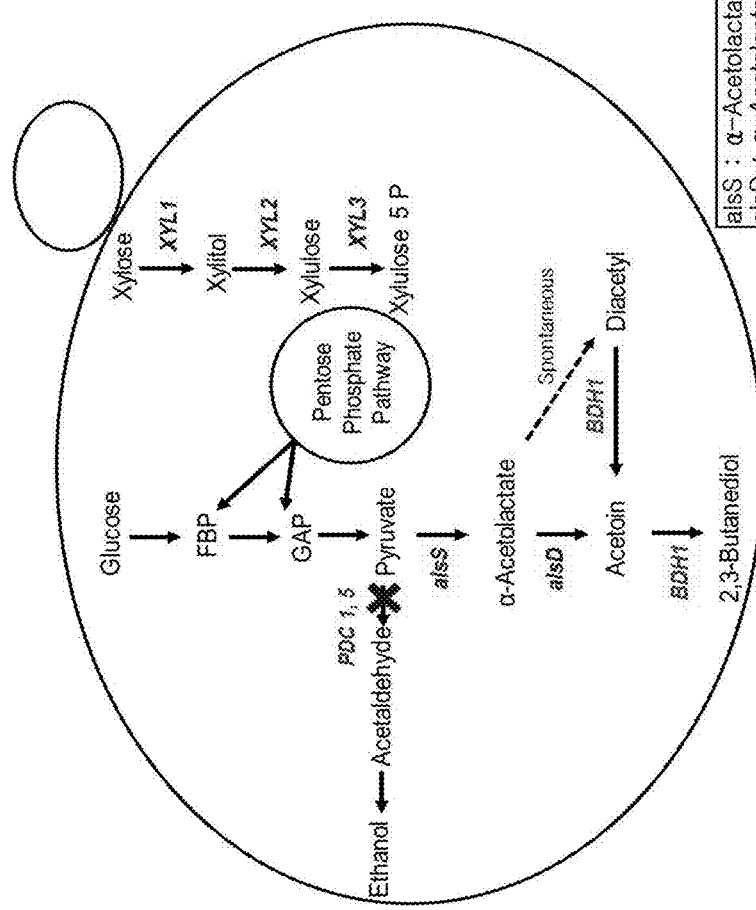

FIG. 13 is a schematic view of metabolic pathway of a recombinant yeast capable of producing 2,3-butanediol.

Figure 14:
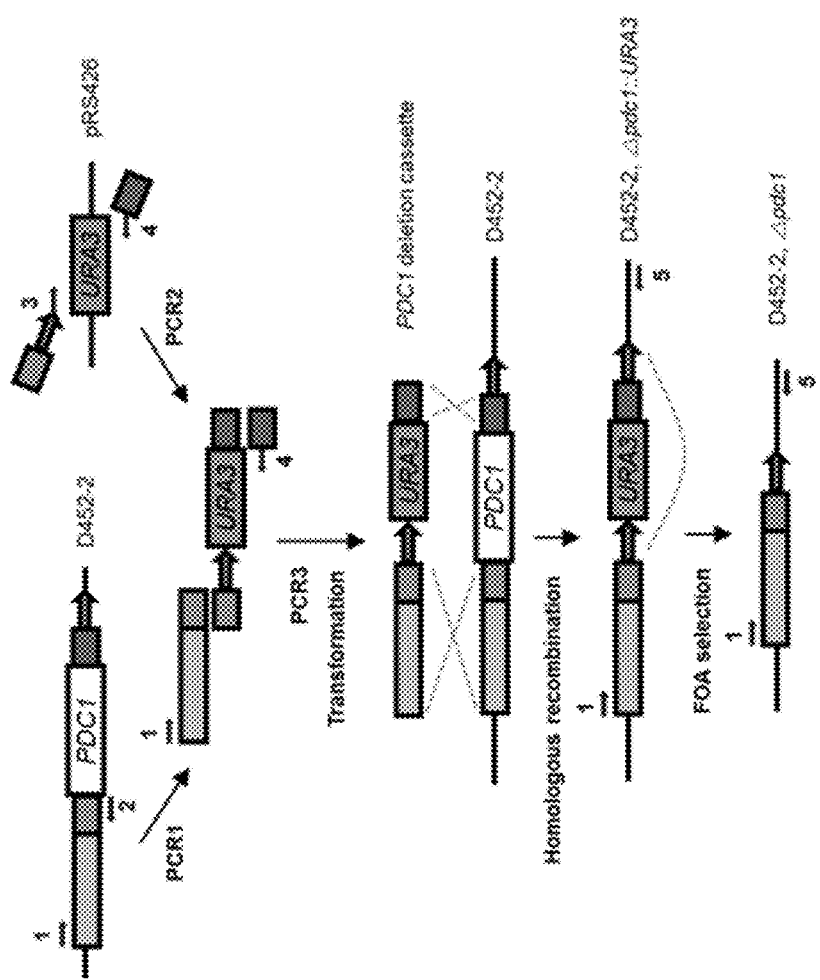

FIG. 14 is a schematic view showing disruption of PDC1 genes by PCR.

DETAILED DESCRIPTION

Ethanol production is considered to be the greatest obstacle to the production of 2,3-butanediol using *Saccharomyces cerevisiae* called yeast. The reason for this is that pyruvate, which is a precursor used for production of 2,3-butanediol, is used for biosynthesis of ethanol rather than 2,3-butanediol (see FIG. 13). In this context, in the present invention, strains lacking pyruvate decarboxylase are used. In addition, strains that are further transformed to express acetolactate synthase, acetolactate decarboxylase and butanediol dehydrogenase are used. In general, in 2,3-butanediol biosynthesis in bacteria, pyruvate is transformed into acetolactate through acetolactate synthase, the acetolactate is then transformed into acetoin through acetolactate decarboxylase, and acetoin is finally transformed into 2,3-butanediol through butanediol dehydrogenase. However, in case of yeast, because yeast has no acetolactate decarboxylase genes, acetolactate is converted into diacetyl through non-enzymatic reaction and the diacetyl is then converted into acetoin and 2,3-butanediol through butanediol dehydrogenase. In addition to these pathways, acetoin may be produced by polymerization of pyruvate or acetaldehyde, but an amount of acetoin is insufficient to produce excess 2,3-butanediol in yeasts (see FIG. 13). Accordingly, there is a need for reinforcing a pathway of producing acetoin from pyruvate via acetolactate.

Consequently, in the present invention, in order to efficiently produce 2,3-butanediol, pyruvate decarboxylase-lacking strains are established to accumulate pyruvate, which is a precursor for 2,3-butanediol biosynthesis, acetolactate synthase and acetolactate decarboxylase are introduced to reinforce a 2,3-butanediol biosynthesis pathway and 2,3-butanediol is efficiently produced from glucose through overexpression of butanediol dehydrogenase in yeasts.

Meanwhile, in the first aspect, function loss of the pyruvate decarboxylase is preferably accomplished by partially disrupting or entirely deleting each of PDC1 gene encoding pyruvate decarboxylase 1 and PDC5 gene encoding pyruvate decarboxylase 5.

*Saccharomyces cerevisiae* has, as isozymes, pyruvate decarboxylase 1, pyruvate decarboxylase 5 and pyruvate decarboxylase 6. However, it is already reported in the art that pyruvate decarboxylase activity is entirely removed only by disrupting PDC1 gene encoding pyruvate decarboxylase 1 and PDC5 gene encoding pyruvate decarboxylase 5. Accordingly, in the present invention, preferably, strains wherein entire pyruvate decarboxylase activity is removed by disruption of PDC1 and PDC5 genes are established.

Meanwhile, in the first aspect of the present invention, the recombinant pyruvate decarboxylase-lacking *Saccharomyces cerevisiae* preferably has MTH1 genes modified such that a glucose-sensing enzyme, Mth1 is not decomposed after phosphorylation by casein kinase I.

The pyruvate decarboxylase-lacking *Saccharomyces cerevisiae* has the following two disadvantages upon use as 2,3-butanediol-producing parent strains. First, production of acetaldehyde, which is a precursor used for synthesis of lysine and fatty acids, is blocked due to enzyme inactivity of pyruvate decarboxylase, $C_2$ compounds (ethanol or acetate) should be added in order to synthesize acetaldehyde so that strains can survive. In addition, these strains should reoxidize NADH accumulated in cells by respiration due to blocked ethanol biosynthesis pathway. However, glucose suppresses expression of respiration-associated enzymes and thus inhibits a respiration process, and as a result, accumulates excess NADH in cells and ultimately delays growth of cells.

Accordingly, in the present invention, solution to this problem is demonstrated to be possible by modifying MTH1 gene such that that a glucose-sensing enzyme, Mth1 is not decomposed after phosphorylation by casein kinase I.

In general, an Mth1 enzyme inhibits transcription of HXT genes encoding hexose transporters involved in introduction of glucose. When glucose is present in extracellular sites, Mth1, is phosphorylated by casein kinase I and is then decomposed. The decomposition of Mth1 restores inhibited transcription of HXT genes and causing glucose to be introduced into cells. Excess glucose introduction causes accumulation of pyruvate in cells and redox imbalance resulting from ethanol synthesis pathway of strains, thus preventing strains from growing in glucose media.

In this regard, according to the present invention, when Mth1 is genetically modified such that the Mth1 is not decomposed after phosphorylation by casein kinase I, the enzyme can be grown even in glucose medium. Genetic modification may be carried out by modifying MTH1 gene such that the Mth1 is not decomposed after phosphorylation by casein kinase I and may be performed by a variety of genetic engineering methods, such as laboratory evolution or point mutation, established in the field to which the present invention pertains.

In an embodiment of the present invention, mutant strains wherein the $241^{st}$ G (base) in MTH1 gene is modified to C (base) by an evolution method based on laboratory evolution and the $81^{st}$ amino acid is thus changed from alanine to proline can be selected. In the present invention, strains that underwent mutations described above are selected by an evolution method based on laboratory evolution. However, because differences in MTH1 genes between mutant strains and parent strains are confirmed through gene analysis according to the present invention, mutant strains having MTH1 gene modified from the $241^{st}$ G (base) to C (base) and the $81^{st}$ amino acid changed from alanine to proline are obtained by applying point mutation to the parent strains.

Meanwhile, in accordance with a second aspect of the present invention, recombinant *Saccharomyces cerevisiae* transformed such that xylose reductase, xylitol dehydrogenase and xylulose kinase are expressed, functions of pyruvate decarboxylase is lost, and acetolactate synthase, acetolactate decarboxylase and butanediol dehydrogenase are expressed.

Comparing with the first aspect, the second aspect is characterized in that *Saccharomyces cerevisiae* is further transformed to express an enzyme required for metabolizing xylose. *Saccharomyces cerevisiae* is used as an ethanol-producing strain for industrial applications, but does not use xylose as a carbon source. The reason for this is that *Saccha-*

*romyces cerevisiae* has neither xylose reductase (XR) nor xylitol dehydrogenase (XDH) and thus has no metabolic activity for converting xylose into xylulose. Accordingly, XR and XDH enzymes should be introduced into *Saccharomyces cerevisiae* in order to produce 2,3-butanediol from xylose. In the *Saccharomyces cerevisiae* transformed by introduction of XR and XDH, xylose is converted into xylulose, the xylulose is converted into xylulose 5-phosphate through further introduced xylulokinase (XK), and metabolism is thus performed via pentose phosphate pathway. XK is an enzyme present in yeast. However, when only XR and XDH are introduced into strains without over-expressing XK, 2,3-butanediol can be produced from xylose, but yield and production efficiency are disadvantageously considerably low. Accordingly, XK is preferably also over-expressed in order to remove these advantages (see FIG. 13).

Meanwhile, in the second aspect of the present invention, function loss of the pyruvate decarboxylase is preferably accomplished by partially disrupting or entirely deleting PDC1 gene encoding pyruvate decarboxylase 1 and PDC5 gene encoding pyruvate decarboxylase 5.

Meanwhile, in the second aspect of the present invention, the pyruvate decarboxylase-lacking *Saccharomyces cerevisiae* capable of metabolizing xylose preferably has MTH1 gene modified such that a glucose-sensing enzyme, Mth1 is not decomposed after phosphorylation by casein kinase I. Detailed operations and effects of genetic modification of MTH1 gene have been sufficiently described with reference to the first aspect of the present invention and are thus omitted.

Meanwhile, in accordance with a third aspect of the present invention, provided is a method of producing 2,3-butanediol comprising inoculating a glucose-containing medium with the recombinant *Saccharomyces cerevisiae* according to the first aspect or recombinant *Saccharomyces cerevisiae* obtained by modifying MTH1 gene of the *Saccharomyces cerevisiae* according to the first aspect such that a glucose-sensing enzyme, Mth1 is not decomposed after phosphorylation by casein kinase I, followed by culturing.

In the present invention, yeasts capable of efficiently producing 2,3-butanediol are established by removing enzymatic activity of the pyruvate decarboxylase and reinforcing the 2,3-butanediol biosynthesis pathway. In particular, 96.2 g/L of 2,3-butanediol is finally produced by fed-batch culture. This result means that 2,3-butanediol can be produced at industrial scale using the recombinant yeast established by the present invention.

Meanwhile, in the third aspect of the present invention, the culturing may be performed while supplying oxygen. Two molecules of NADH are produced during glycolysis in the production of 2,3-butanediol from glucose, but only one molecule thereof is converted for production of 2,3-butanediol, thus causing redox imbalance. Accordingly, oxygen supply for NADH reoxidation is a major factor in producing 2,3-butanediol. As can be seen from experiments performed by the present invention, as supply of oxygen increases, glucose consumption rate and cell growth increase and production efficiency of 2,3-butanediol is increased. However, acetoin, rather than 2,3-butanediol, is obtained as a major product when excess oxygen is supplied. For this reason, optimal oxygen supply is required.

Meanwhile, in the third aspect of the present invention, the culturing is preferably fed-batch culturing including continuously supplying glucose. Production of 2,3-butanediol can be increased by fed-batch culturing including continuously supplying a substrate.

Meanwhile, in accordance with a fourth aspect of the present invention, provided is a method of producing 2,3-butanediol comprising inoculating a glucose-containing medium with the recombinant *Saccharomyces cerevisiae* according to the second aspect or recombinant *Saccharomyces cerevisiae* obtained by modifying MTH1 gene of the *Saccharomyces cerevisiae* according to the second aspect such that a glucose-sensing enzyme, Mth1 is not decomposed after phosphorylation by casein kinase I, followed by culturing.

In the present invention, in an attempt to produce 2,3-butanediol from xylose, which is a more economical substrate than glucose, strains accumulating pyruvate, which is a major precursor of 2,3-butanediol, from xylose are established by introducing xylose metabolism genes into yeasts wherein enzymatic activity of pyruvate decarboxylase is removed, and yeasts capable of efficiently producing 2,3-butanediol from xylose are established by reinforcing the 2,3-butanediol biosynthesis pathway. It can be seen that these yeasts enable production of about 20 g/L of 2,3-butanediol from about 80 g/L of xylose. In addition, it can be seen that 52.2 g/L of 2,3-butanediol can be produced from a mixture of glucose and xylose by fed-batch culture. In addition, only (R,R)-2,3-butanediol among 2,3-butanediol isomers is selectively produced as 2,3-butanediol. This result indicates that 2,3-butanediol can be economically produced based on lignocellulosic biomass using the recombinant yeast of the present invention.

Meanwhile, in the fourth aspect of the present invention, the medium preferably further contains glucose. Preferably, growth of culture strains can be further facilitated by adding glucose to a medium containing xylose.

Meanwhile, in the fourth aspect of the present invention, the culturing is preferably carried out while supplying oxygen. A technical meaning associated with restoration of redox balance caused by oxygen supply has been described with reference to the third aspect of the present invention and a detailed explanation thereof is thus omitted.

Meanwhile, in the fourth aspect of the present invention, the culturing is preferably fed-batch culturing including continuously supplying glucose. Production of 2,3-butanediol can be increased by fed-batch culturing including continuously supplying a substrate.

Meanwhile, in the fourth aspect of the present invention, when glucose is further contained in the medium, the culturing is preferably fed-batch culturing including continuously supplying xylose and glucose. By continuously supplying xylose and glucose, production efficiency of 2,3-butanediol is improved and continuous growth of strains is possible.

Figure 2:
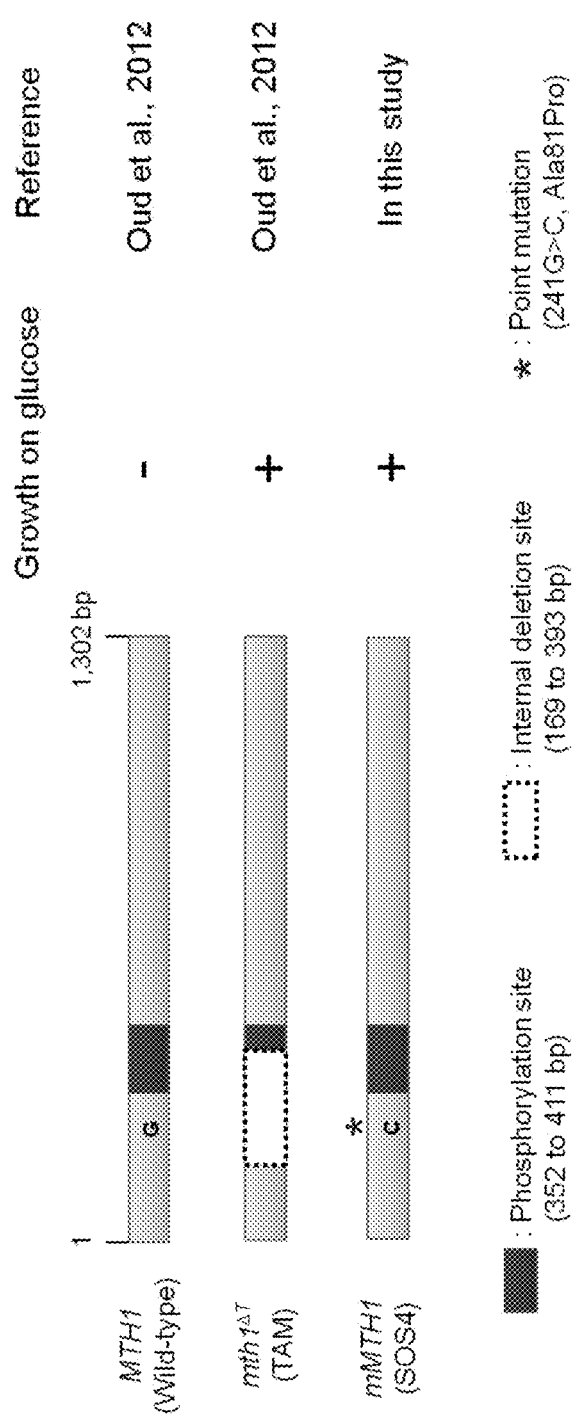
FIG. 2 shows results of comparison between MTH1 gene mutants of two pyruvate decarboxylase-lacking strains (TAM and SOS4 strains) capable of metabolizing glucose.
Figure 3:
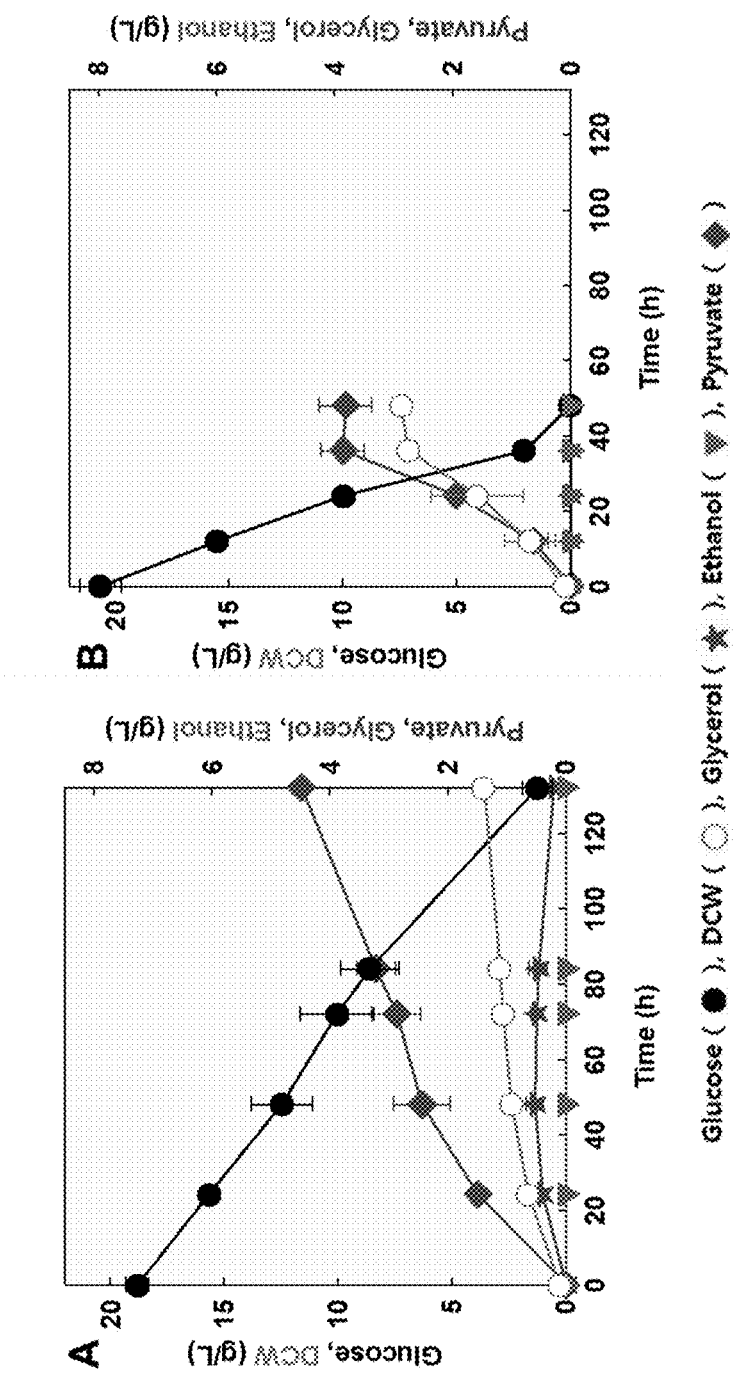
FIG. 3 shows fermentation behaviors of SOS4 strains in (A) YP medium containing 2% glucose under microaerobic conditions and (B) YP medium containing 2% glucose under aerobic conditions.

In the present invention, a recombinant yeast capable of producing 2,3-butanediol at high production efficiency is developed using a metabolic engineering technology as depicted by FIG. 13, and 2,3-butanediol is produced at high production efficiency from glucose or xylose using the recombinant yeast.

First, in order to inhibit production of ethanol which is a major by-product of yeasts, PDC1 and PDC5 genes encoding pyruvate decarboxylase are disrupted.

In addition, in order to avoid inefficient biosynthesis pathway of 2,3-butanediol, acetolactate synthase and acetolactate decarboxylase genes derived from *Bacillus subtilis* are introduced and butanediol dehydrogenase genes in yeasts are further over-expressed.

In addition, strains capable of producing 2,3-butanediol from xylose at a high yield are established by introducing xylose reductase, xylitol dehydrogenase and xylulose kinase which are xylose metabolism-associated genes to use xylose as a lignocellulosic biomass-derived substrate.

Results of culture (batch-culture and fed-batch culture) of strains established by the present invention are summarized in TABLE 1 below.

TABLE 1

Production of 2,3-BD using established recombinant Saccharomyces cerevisiae

| Strains (properties of strains) | Culture method | Carbon source | 2,3-BD production (g/L) | 2,3-BD yield (g 2,3-BD/ g carbon source) | 2,3-BD productivity (g/L · h) |
|---|---|---|---|---|---|
| BD4 lack of pyruvate decarboxylase over-expression of alsS, alsD and BDH1 genes | Batch-culture | Glucose | 34.8 | 0.36 | 0.32 |
| | Fed-batch culture | Glucose | 96.2 | 0.28 | 0.39 |
| BD4X lack of pyruvate decarboxylase Introduction of XYL1, XYL2, XYL3 genes over-expression of alsS, alsD, BDH1 genes | Batch-culture | Xylose | 20.7 | 0.27 | 0.18 |
| | Fed-batch culture | Glucose[1] xylose | 43.6 | 0.25 | 0.16 |
| | | Glucose[2] xylose | 49.6 | 0.26 | 0.19 |

[1]Glucose-limited xylose fed-batch culture
[2]Glucose and xylose are simultaneously supplied at high concentration

EXAMPLES

Hereinafter, the present invention will be described in more detail with reference to the following Examples. The scope of the present invention is not limited to the following examples and covers modifications of the technical spirit substantially equivalent thereto.

Example 1

Strains (SOS4) Accumulating Pyruvate from Glucose without Producing Ethanol by Disrupting PDC1 and PDC5 Genes (1) Introduction Introduction of biosynthesis pathway of bacteria-derived 2,3-butanediol into wild yeasts ineffectively has a relatively low 2,3-butanediol yield due to production of ethanol.

Accordingly, the present inventors established parent strains (SOS2) capable of blocking ethanol biosynthesis pathway of yeasts and thus accumulating pyruvate as a 2,3-butanediol precursor for efficient production of 2,3-butanediol. In addition, the present inventors established pyruvate decarboxylase-lacking strains (SOS4) metabolizing glucose.

(2) Materials and Methods

1. Strains and Plasmids

*Saccharomyces cerevisiae* D452-2 was used as parent strains for producing pyruvate decarboxylase-lacking strains (SOS2) and pyruvate decarboxylase-lacking strains (SOS4) capable of metabolizing glucose. *Escherichia coli* Top 10 was used for gene manipulation. Primers for producing the strains, plasmids, and PDC1 and PDC5-lacking strains used for the present testing are shown in Tables 2 and 3.

TABLE 2

Strains and plasmids used in the present invention

| Names | Details | Origin |
|---|---|---|
| Strains | | |
| D452-2 | *Saccharomyces cerevisiae*, MAT, leu2, his3, ura3 and can1 | Hosaka, 1992[a] |
| SOS2 | D452-2 Δpdc1, Δpdc5 | Present study |
| SOS4 | D452-2 Δpdc1, Δpdc5 (strains derived from C$_2$-independent high-concentration glucose) | Present study |
| SOS4X | SOS4 ura3::URA3 pSR6-X123 | Present study |
| CON | SOS4 (pRS426GPD, pRS423GPD, pRS425GPD) | Present study |
| BD4 | SOS4 (pRS426_AlsS, pRS423_AlsD, pRS425_BDH1) | Present study |
| CON-X | SOS4X (pRS423GPD, pRS425GPD) | Present study |
| BD4X | SOS4X (pRS423_AlsS_AlsD, pRS425_BDH1) | Present study |
| Plasmids | | |
| pRS426GPD | URA3, GPD promoter, CYC1 terminator, 2μ origin, Amp$^r$ | Christianson, 1992[b] |
| pRS423GPD | HIS3, GPD promoter, CYC1 terminator, 2μ origin, Amp$^r$ | Christianson, 1992[b] |
| pRS425GPD | LEU2, GPD promoter, CYC1 terminator, 2μ origin, Amp$^r$ | Christianson, 1992[b] |
| pRS306 | URA3, 2μ origin, Amp$^r$ | Sikorski and Hieter, 1989[c] |
| pRS426_AlsS | *Bacillus subtilis* str. 168-derived alsS gene contained in pRS426GPD plasmid | Present study |
| pRS423_AlsD | *B. subtilis* str. 168-derived alsD gene contained in pRS423GPD plasmid | Present study |
| pRS423_AlsS_AlsD | *B. subtilis* str. 168-derived alsS, alsD gene contained in pRS423GPD plasmid | Present study |
| pRS425_BDH1 | *S. cerevisiae* D452-2-derived BDH1 gene contained in pRS425GPD plasmid | Present study |
| pSR6-X123 | pRS306 TDH3$_P$-XYL1-TDH3$_T$, PGK1$_P$-XYL2-PGL1$_T$, TDH3$_P$-XYL3-TDH3$_T$ | Kim et al. 2012[d] |

[a]Hosaka, K., Nikawa, J., Kodaki, T., Yamashita, S., (1992) A dominant mutation that alters the regulation of INO1 expression in *Saccharomyces cerevisiae*. Journal of Biochemistry-Tokyo 111, 352-358.
[b]Christianson, T. W., Sikorski, R. S., Dante, M., Shero, J. H., Hieter, P., (1992) Multifunctional yeast high-copy number shuttle vectors. Gene 110, 119-122.
[c]Sikorski, R. S. and Hieter, P., (1989) A system of shuttle vectors and yeast host strains designed for efficient manipulation of DNA in *Saccharomyces cerevisiae*. Gene 122, 19-27.
[d]Kim, S. R., Ha, S. J., Kon, I. I., Jin, Y. S., (2012) High expression of XYL2 coding for xylitol dehydrogenase is necessary for efficient xylose fermentation by engineered *Saccharomyces cerevisiae*. Metabolic Engineering 14, 336-343.

TABLE 3

Primers used in the present invention (underlined parts indicate restriction enzyme sites)

| Target DNA (restriction enzyme) | Base sequence | SEQ ID NO: |
|---|---|---|
| PDC1 disruption | | |
| F-d_PDC1-1(XbaI) | GC<u>TCTAGA</u>CTTGAAAAAGGAACAAGCTC | 1 |
| R-d_PDC1-2 | GATTTGACTGTGTTATTTTG | 2 |
| F-d_PDC1-3(AscI) | CAAAATAACACAGTCAAAT<u>CGGCGCGCC</u>TTTTTATGTAACGAAAAATAAATTGGTTCATATTATTACTGATTCGGTAATCTCCGA | 3 |

TABLE 3-continued

Primers used in the present invention (underlined parts indicate restriction enzyme sites)

| Target DNA (restriction enzyme) | Base sequence | SEQ ID NO: |
|---|---|---|
| R-d_PDC1-4 (XbaI) | GCTCTAGATGCTTATAAAACTTTAACTAATAATTAGAGATTAAATCGCGGGTAATAACTGATATAATTA | 4 |
| R-d_PDC1-check | GACTGTCGGCAACTTCTTG | 5 |
| PDC5 disruption | | |
| F_d_PDC5-1 (XbaI) | GCTCTAGAAGGTTCAAAGACTCTATAAG | 6 |
| R-d_PDC5-2 | GTTCTTCTTGTTATTGTATTG | 7 |
| F-d_PDC5-3 (AscI) | CAATACAATAACAAGAAGAACGGCGCGCCTAGTATAATAAATTTCTGATTTGGTTTAAAATATCAACTAGATTCGGTAATCTCCGAA | 8 |
| R-d_PDC5-4 (XbaI) | GCTCTAGACTATATCTATGCCAATTATTTACCTAAACATCTATAACCTGGGTAATAACTGATATAATTA | 9 |
| R-d_PDC5-check | AGGTACAAAACCGAATACG | 10 |
| Gene replication | | |
| F_AlsS (BamHI) | CGGGATCCATGTTGACAAAAGCAACAAAAGA | 11 |
| F_AlsD (BamHI) | CCGCTCGAGCTAGAGAGCTTTCGTTTTCA | 12 |
| R_AlsD (XhoI) | CCGCTCGAGTTATTCAGGGCTTCCTTCAG | 13 |
| F_BDH1 (BamHI) | CGGGATCCAAAATGAGAGCTTTGGCATATTTC | 14 |
| R_BDH1 (XhoI) | CCGCTCGAGTTACTTCATTTCACCGTGATTG | 15 |

2. Medium and Culture Conditions

*Escherichia coli* was cultured in a Lysogeny broth (LB) medium containing 50 μg/mL of ampicillin, and yeast was cultured in a YP (10 g/L of yeast extract, 20 g/L of Bacto peptone) medium containing 2% (w/v) glucose. A YSC (6.7 g/L Yeast Nitrogen Base (YNB), 2% glucose, suitable amino acid) medium was used as a selection medium to select transformed yeasts.

3. Yeast Transformation

Insertion of cassettes for disrupting pyruvate decarboxylase enzyme-associated genes and plasmids for over-expressing 2,3-butanediol biosynthesis genes was performed using an EZ-Transformation kit (BIO 101, Vista, Calif.) and selection was performed in a YSC medium. An FOA medium was used for reproduction of URA markers in the production of pyruvate decarboxylase-lacking strains.

4. Disruption of PDC1 and PDC5 Genes and Laboratory Evolution

Disruption of PDC1 and PDC5 genes was performed using similar base sequences amplified by PCR and a URA3 marker collection method. The disruption process is shown in FITG. 14.

PDC1 and PDC5 gene disruption cassettes were acquired by PCR using primers shown in Table 3 above and transformants wherein PDC1 gene is disrupted by insertion of disruption cassettes were selected in a YSC selection medium wherein uracil amino acid was removed. These transformants were cultured in a YP medium for 24 hours and were then cultured on an FOA plate for collecting URA3 markers. SOS2 strains wherein activity of pyruvate decarboxylase was removed were established by further disrupting PDC5 genes of the marker-collected PDC1-disrupted strains in the same manner as above.

Meanwhile, in order to obtain pyruvate decarboxylase-lacking strains independent of $C_2$ compounds, strains were passage-cultured while gradually decreasing an amount of acetate as a $C_2$ compound. In addition, in order to transform these strains into pyruvate decarboxylase-lacking strains capable of metabolizing high-concentration glucose, evolved strains independent of a $C_2$ compound were passage cultured while gradually increasing an amount of glucose in the medium. Passage culture was performed 10 times in total. As a result, pyruvate decarboxylase-lacking strains (SOS4) capable of metabolizing high-concentration glucose, independent of $C_2$ compound were established.

(3) Results

Strains (SOS2) wherein enzymatic activity of pyruvate decarboxylase was removed were established by disrupting PDC1 and PDC5 genes so as to block the ethanol biosynthesis pathway. However, SOS2 strains could not be grown in a glucose medium and were grown only in a medium containing a $C_2$ compound such as acetate or ethanol.

In order to solve these problems, pyruvate decarboxylase-lacking strains (SOS4) which are independent of $C_2$ compound and are viable in glucose are selected using an evolution method to decrease a concentration of $C_2$ compound in a medium and to increase a concentration of glucose therein.

Figure 1:
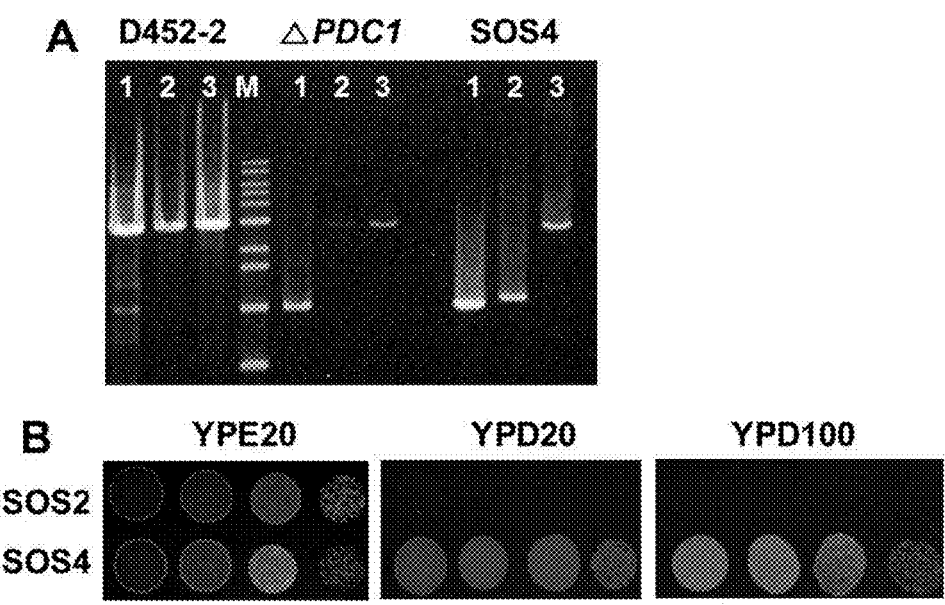
FIG. 1A is an image showing disruption of PDC1 and PDC5 genes in SOS4 strains, wherein the disruption of PDC1 and PDC5 genes is confirmed from shortened PCR fragments of SOS4 strains (No. 1: PDC1 gene PCR fragment, No. 2: PDC5 gene PCR fragment, No. 3: PDC6 gene PCR fragment, and M: size marker).
FIG. 1B is an image showing pyruvate decarboxylase-lacking strains (SOS2) and pyruvate decarboxylase-lacking strains (SOS4) capable of metabolizing glucose (YPE20: YP medium containing 2% ethanol, YPD20: YP medium containing 2% glucose, YPD100: YP medium containing 10% glucose)

FIG. 1A is an image showing disruption of PDC1 and PDC5 genes in SOS4 strains, wherein the disruption of PDC1 and PDC5 genes is confirmed from shortened PCR fragments of SOS4 strains (No. 1: PDC1 gene PCR fragment, No. 2: PDC5 gene PCR fragment, No. 3: PDC6 gene PCR fragment, and M: size marker). In FIG. 1A, ΔPDC1 is a strain wherein only PDC1 genes are disrupted and SOS4 is a stain wherein both PDC1 and PDC5 genes are disrupted.

As can be seen from FIG. 1B, SOS2 strains are grown in an ethanol medium, but are not grown in 2%(w/v) and 10%(w/v) glucose media, while SOS4 strains are grown in an ethanol medium as well as a glucose medium. FIG. 1B is an image showing growth of SOS4 strains evolved from SOS2 strains (YPE20: YP medium containing 2% ethanol, YPD20: YP medium containing 2% glucose, YPD100: YP medium containing 10% glucose).

Example 2

Gene Analysis of Pyruvate Decarboxylase-Lacking Strains (SOS4) Having Improved Glucose Metabolism Function Independent of C2 Compound, Established in Example 1

(1) Introduction

Next generation genome sequencing was performed to find genetic modification contributing to characters of independence from $C_2$ compound and improved glucose metabolism function in SOS4 strains.

(2) Materials and Methods

Genomic DNAs were extracted from wild yeasts D452-2 and pyruvate decarboxylase-lacking strains (SOS4) evolved so that they can metabolize glucose, and base sequences of the genomes were compared. Shotgun DNAseq libraries were made using a TruSeq DNAseq sample prep kit and were assayed by qPCR and gene base sequence analysis was then performed using a TruSeq SBS sequencing kit.

(3) Results

It was confirmed in SOS4 strains that the $241^{st}$ G base of MTH1, gene controlling glucose sensing, was modified to a C base and the $81^{st}$ amino acid was thus changed from alanine to proline.

In general, an Mth1 enzyme inhibits transcription of HXT genes encoding hexose transporters involved in introduction of glucose. When glucose is present in extracellular sites, Mth1 is phosphorylated by casein kinase I and is then decomposed. The decomposition of Mth1 restores inhibited transcription of HXT genes, thus causing glucose to be introduced into cells. Excess glucose introduction causes accumulation of pyruvate in cells and redox imbalance resulting from ethanol synthesis pathway of strains, thus preventing strains from growing in glucose medium.

On the other hand, in case of the Mth1 mutant strain, SOS4 established by the present invention, Mth1 is not decomposed due to modification of Mth1 enzyme although glucose is present in extracellular sites. For this reason, transcription of HXT genes is not restored and inflow of glucose slowly proceeds. The delayed inflow of glucose reduces accumulation of pyruvate in cells and redox imbalance which results from blocking of ethanol synthesis pathway, and enables SOS4 strains to be slowly grown in a glucose medium.

As can be seen from a recently reported research, removal of bases present in portions including phosphorylation sites and PEST sites associated with decomposition of the Mth1 enzyme of pyruvate decarboxylase-lacking strains (TAM) having reduced growth inhibition in glucose inhibits decomposition of the Mth1 enzyme, thus eliminating glucose metabolism inhibition activity of Mth1 mutant strains. It may be thought that, similar to this, modification of the $241^{st}$ base and thus variation in amino acid found by the present inventors also inhibits decomposition of Mth1 and provides improvement in glucose metabolism performance independent of $C_2$.

FIG. 2 shows results of comparison between MTH1 gene mutants of two pyruvate decarboxylase-lacking strains (TAM and SOS4 strains) having glucose resistance.

Example 3

Confirmation of Accumulation of Pyruvate in SOS4 Strains (1) Introduction

In order to confirm growth of SOS4 and accumulation of pyruvate therein, SOS4 strains were batch-cultured under microaerobic and aerobic conditions in a YP medium containing 2% glucose.

(2) Materials and Methods

Pre-culture was performed in 5 mL of a selection medium (YSC) containing 2% (w/v) glucose for fermentation testing using a flask. Cells were inoculated in 50 mL of a YP medium containing 2% (w/v) or 10% (w/v) glucose at an initial OD of 1 and were then batch-cultured. A stirring rate was maintained at 80 rpm for microaerobic conditions.

(3) Results

SOS4 strains consumed 2% glucose over 120 hours under microaerobic conditions and accumulated about 4.5 g/L of pyruvate in the medium, while they consumed glucose more rapidly under aerobic conditions and accumulated about 4 g/L of pyruvate. Accumulation of pyruvate and inhibition of ethanol production in SOS4 strains mean that enzymatic activity of pyruvate decarboxylase is completely removed.

FIG. 3 shows fermentation behaviors of SOS4 strains, wherein FIG. 3A shows fermentation behaviors in a YP medium containing 2% glucose under microaerobic conditions, and FIG. 3B shows fermentation behaviors in a YP medium containing 2% glucose under aerobic conditions.

Example 4

2,3-Butanediol of Pyruvate Decarboxylase-Lacking Yeast (BD4) Reinforced with 2,3-Butanediol Biosynthesis Pathway (1) Introduction Because SOS4 strains did not produce ethanol and accumulated pyruvate, alsS and alsD genes derived from *Bacillus subtilis* were introduced and BDH1 genes in yeasts were overexpressed, thereby reinforcing 2,3-butanediol biosynthesis pathway, so as to efficiently convert accumulated pyruvate into 2,3-butanediol.

(2) Materials and Methods

Primers for replicating 2,3-butanediol biosynthesis genes, i.e., alsS, alsD and BDH1 were shown in Tables 2 and 3 above. pRS426_alsS, pRS423_alsD and pRS425_BDH1 plasmids comprising alsS, alsD and BDH1 genes were introduced (transduced) into SOS4 strains under control of constitutive expression GPD promoters. *Escherichia coli* Top 10 was used for gene manipulation.

(3) Results

BD4 strains into which alsS, alsD and BDH1 genes were introduced were established by the method above and these strains produced about 6 g/L of 2,3-butanediol from 20 g/L of glucose within 32 hours without producing ethanol. In addition, the BD4 strains exhibited a glucose consumption rate 4 or more times that of a control group. To increase an amount of 2,3-butanediol, batch-culture was performed in a YP medium containing 10% glucose. As a result, BD4 strains consumed 100 g/L of glucose over 120 hours and produced about 32 g/L of 2,3-butanediol at a high yield (0.34 g 2,3-butanediol/g glucose) and production efficiency (0.26 g/Lh).

Figure 4:
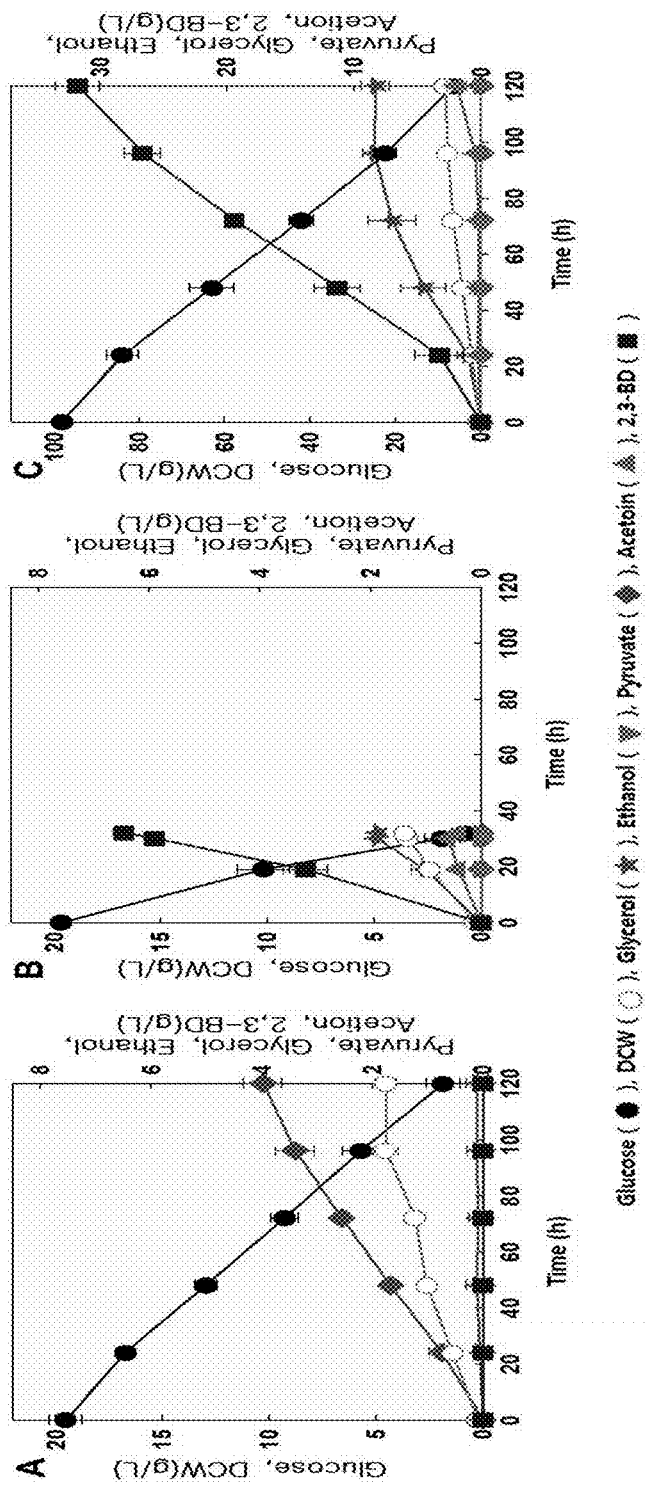
FIG. 4 shows results of comparison in glucose consumption and 2,3-butanediol production between BD4 strains and control strains under microaerobic conditions. (A): control group in a 2% glucose-containing YP medium, (B): BD4 in a 2% glucose-containing YP medium and (C): BD4 in a 10% glucose-containing YP medium.

FIG. 4 shows results of comparison in glucose consumption and 2,3-butanediol production between BD4 and control strains under microaerobic conditions, wherein FIG. 4A shows a control group in a 2% glucose-containing YP medium, FIG. 4B shows BD4 in a 2% glucose-containing YP medium and FIG. 4C shows BD4 in a 10% glucose-containing YP medium.

Example 5

Determination of Effects of Oxygen Supply on 2,3-Butanediol Production (1) Introduction Two molecules of NADH were produced during glycolysis from glucose, but only one molecule was converted for production of 2,3-butanediol, thus resulting in redox imbalance. Accordingly, oxygen supply for reproduction of $NAD^+$ through NADH reoxidation is considered to be a major factor in 2,3-butanediol production. In particular, inhibitory action on glycerol production under aerobic condition means that NADH reoxidation in the cytoplasm is caused by respiration increased by oxygen.

Accordingly, optimal oxygen conditions were searched to efficiently produce 2,3-butanediol by inhibition on production of by-products such as glycerol and acetoin. In order to study correlation between oxygen supply and 2,3-butanediol production, batch-culture was performed under various oxygen supply conditions after supply of 100 g/L of glucose.

(2) Materials and Methods

Various concentrations of oxygen were supplied to a fermentor via combination of amount of supplied oxygen (0, 0.25, 1 vvm) and stirring rate (300, 500 rpm). Batch-culture under various oxygen supply conditions was performed in a 1 L fermentor while maintaining a pH of 5.5 and a temperature of 30° C. Strains were inoculated at an initial OD of 1 in 500 mL of a YP medium containing 10% (w/v) glucose using the established BD4 strains.

(3) Results

Figure 5:
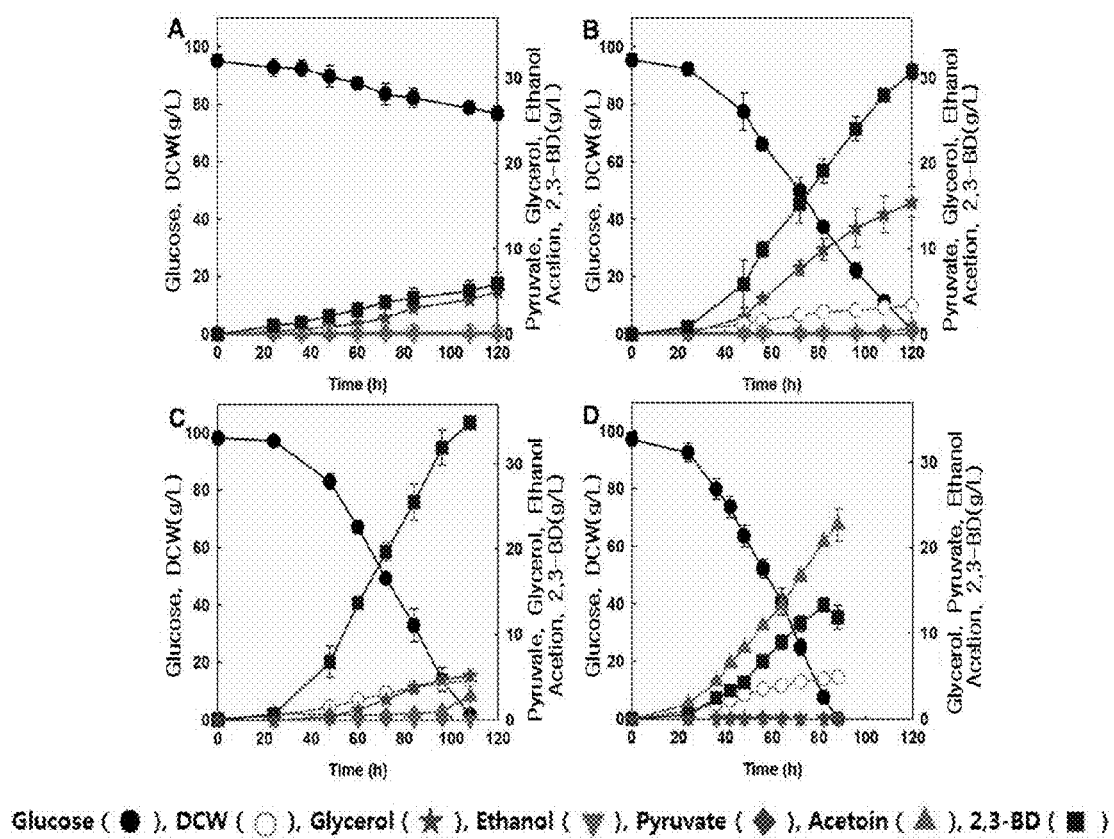
FIG. 5 shows fermentation behaviors of BD4 under various oxygen conditions. (A) 0 vvm, 300 rpm, (B) 0.25 vvm, 300 rpm, (C) 1.0 vvm, 300 rpm, (D) 1.0 vvm, 500 rpm.

It can be seen from FIG. 5 that glucose consumption rate increases and cell growth is facilitated, as supply of oxygen increases. About 35 g/L of 2,3-butanediol was produced at the highest yield (0.36 g 2,3-butanediol/g glucose) and the highest production efficiency (0.32 g/L-h) under oxygen supply conditions of 300 rpm and 1 vvm, among the various oxygen conditions. FIG. 5 shows fermentation behaviors of BD4 under various oxygen conditions. (A) 0 vvm, 300 rpm, (B) 0.25 vvm, 300 rpm, (C) 1.0 vvm, 300 rpm, (D) 1.0 vvm, 500 rpm.

Example 6

Production of 2,3-Butanediol by Fed-Batch Culture (1) Introduction

Fed-batch culture through intermittent glucose addition (glucose dumping) was performed to determine whether or not BD4 strains are suitable as 2,3-butanediol-producing strains.

(2) Materials and Methods

Fed-batch culture was performed to obtain high-concentration 2,3-butanediol. The fed-batch culture was performed using a 1 L fermentor while maintaining a pH at 5.5 and a temperature at 30° C. BD4 strains were inoculated in a 500 mL of a YP medium containing 10% (w/v) glucose at an initial OD of 10 and glucose was continuously supplied at a concentration of 100 g/L using 800 g/L of a glucose solution when glucose was consumed.

(3) Results

Figure 6:
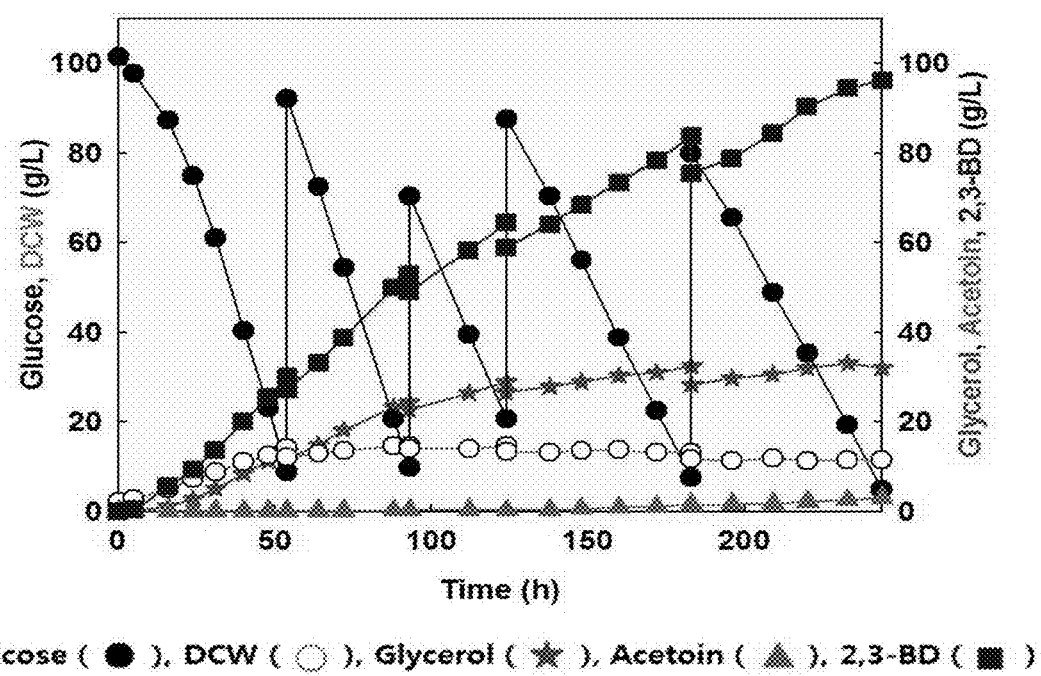
FIG. 6 shows results of fed-batch culture of BD4 strains.

For a culture time of 244 hours, about 96.2 g/L of 2,3-butanediol was produced at a yield of 0.28 g 2,3-butanediol/g glucose and a production efficiency of 0.39 g/Lh, which demonstrates that the BD4 strains are suitable as 2,3-butanediol-producing strains. FIG. 6 shows results of fed-batch culture of BD4 strains.

Example 7

Establishment of Yeast Strain (SOS4X) Accumulating Pyruvate by Metabolizing Xylose (1) Introduction Strains (SOS4X) capable of accumulating pyruvate from xylose were established by introducing XYL1, XYL2 and XYL3 encoding *Scheffersomyces stipites*-derived xylose metabolism enzymes, i.e., xylose reductase, xylitol dehydrogenase and xylulose kinase, into parent strains, i.e., SOS4.

(2) Materials and Methods (a) Strains and Plasmids

SOS4X strains were established by inserting vectors (pSR6-X123), wherein XYL1, XYL2 and XYL3 genes derived from *Scheffersomyces stipites* are inserted into pyruvate decarboxylase-lacking strains (SOS4) derived from *Saccharomyces cerevisiae* D452-2, into URA marker sites of genomic DNAs (see Table 2 above). *Escherichia coli* Top 10 was used for gene manipulation.

(b) Medium and Culture Conditions

*Escherichia coli* (*E. coli*) was cultured in a LB medium containing 50 μg/mL of ampicillin and yeast was cultured in a YP medium containing 4% xylose. The culture was performed in a YP medium containing 2% glucose and 8% xylose for fermentation of mixed sugar. A YSC medium was used as a selection medium to select transformed yeast.

(c) Yeast Transformation

Introduction of xylose metabolism-associated genes and insertion of plasmids for over-expression of 2,3-butanediol biosynthesis genes were performed using "EZ-Transformation kit (BIO 101, Vista, Calif.)" and selection was performed in a YSC medium.

(3) Results

Figure 7:
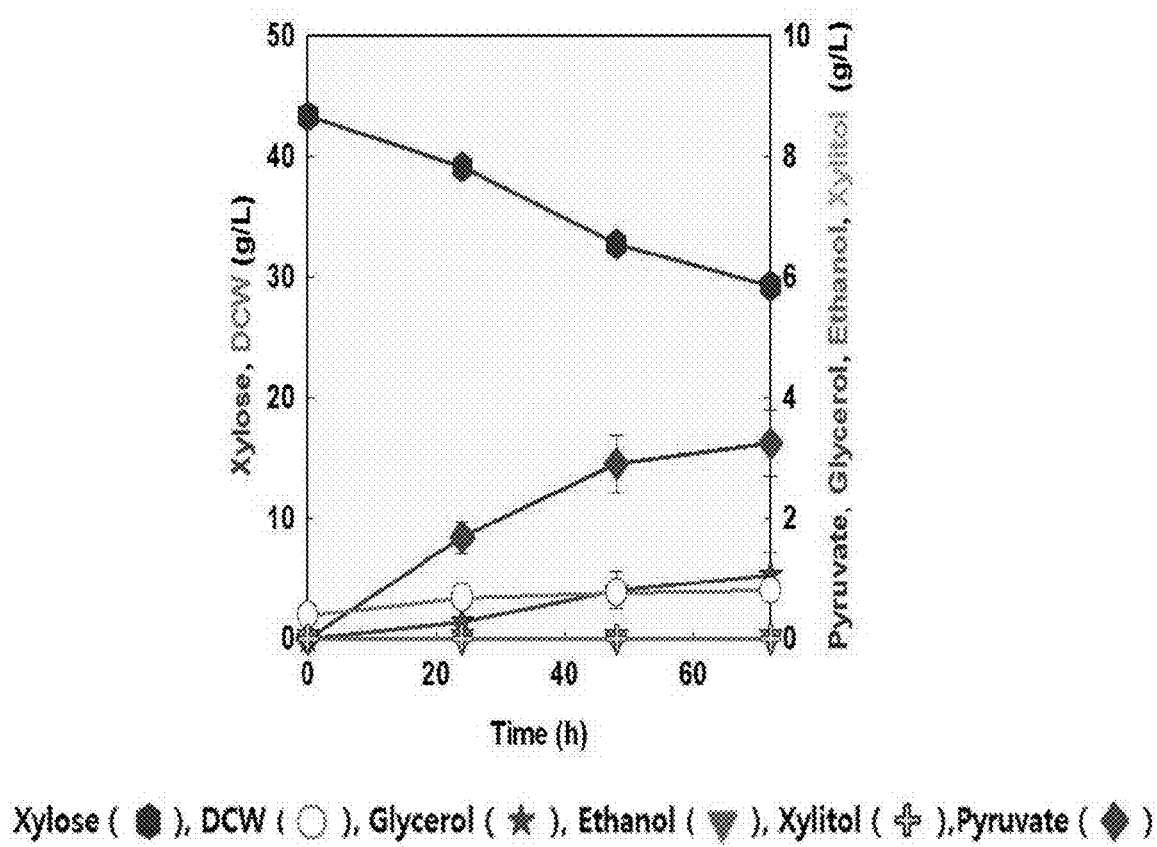
FIG. 7 shows fermentation behaviors of SOS4X strains in a YP medium containing xylose.

SOS4X strains consumed 14 g/L in 40 g/L of xylose over 72 hours and accumulated 3.2 g/L of pyruvate in a medium. FIG. 7 shows fermentation behaviors of SOS4X strains in a YP medium containing xylose.

Example 8

Production of 2,3-Butanediol from Xylose by Pyruvate Decarboxylase-Lacking Yeasts (BD4X) Involving 2,3-Butanediol Biosynthesis Pathway and Thus Capable of Metabolizing Xylose (1) Introduction SOS4X strains accumulated pyruvate from xylose as described above. 2,3-butanediol-producing strains (BD4X) were established using the strains and whether or not 2,3-butanediol was produced was confirmed.

(2) Materials and Methods

BD4X strains capable of producing 2,3-butanediol from xylose were established by introducing pRS423_AlsS_AlsD and pRS425_BDH1 plasmids comprising alsS, alsD and BDH1 genes into SOS4 strains under control of constitutive expression promoters for 2,3-butanediol production (see Table 2 above).

Pre-culture was performed in a selection medium (YSC) containing 2% (w/v) glucose for fermentation testing using a flask. Cells were inoculated in 50 mL of a YP medium containing 2% (w/v) or 10% (w/v) glucose at an initial OD of and were then main-cultured. A stirring rate was maintained at 80 rpm for microaerobic conditions.

(3) Results

Figure 8:
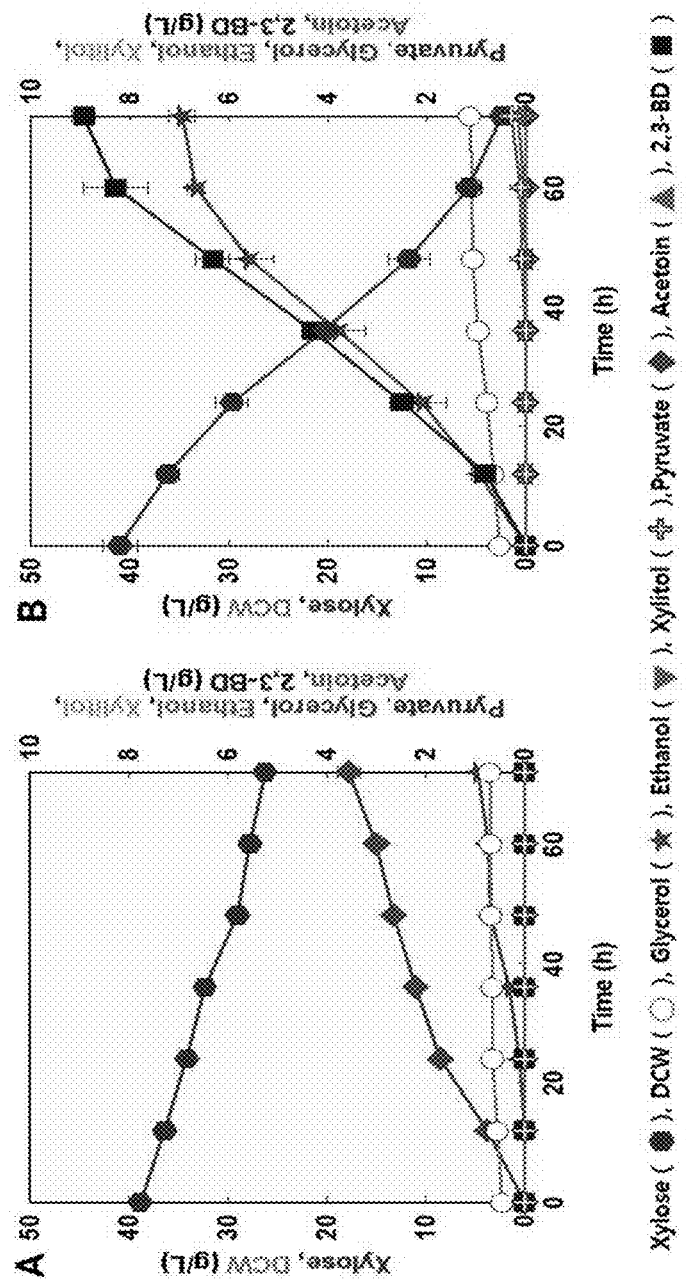
FIG. 8 shows results of production of 2,3-butanediol from xylose by BD4X strains under microaerobic conditions. (A): control group (CON-X) in a YP medium containing 4% xylose and (B): BD4X in a YP medium containing 4% xylose.

Control strains (CON-X) metabolized about 12 g/L of xylose among 40 g/L of xylose for 72 hours and thus accumulated 3.6 g/L of pyruvate, while BD4X strains involving 2,3-butanediol biosynthesis pathway consumed most of xylose and produced 9 g/L of 2,3-butanediol. This means that accumulated pyruvate was efficiently converted into 2,3-butanediol due to 2,3-butanediol biosynthesis pathway, and speed of xylose metabolism was improved. FIG. 8 shows results of production of 2,3-butanediol from xylose by BD4X strains under microaerobic conditions, wherein FIG. 8A shows fermentation behaviors of control group (CON-X) in a YP medium containing 4% xylose and FIG. 8B shows fermentation behaviors of BD4X in a YP medium containing 4% xylose.

Example 9

Production of 2,3-Butanediol from High-Concentration Xylose and Mixed Sugar of Glucose and Xylose by BD4X Strains (1) Introduction Variation in production of 2,3-butanediol using, as a substrate, high-concentration xylose or mixed sugar of glucose and xylose was confirmed so as to increase an amount of 2,3-butanediol.

(2) Materials and Methods

Batch-culture was performed in a YP medium containing 8% (w/v) xylose in order to confirm behaviors of production of 2,3-butanediol from high-concentration xylose. In addition, mixed sugar of 8% (w/v) xylose and 2% (w/v) glucose was used for mixed sugar fermentation.

(3) Results

Batch-culture was performed in a YP medium containing 8% xylose. As a result, BD4X strains consumed most of supplied xylose over 120 hours and thus produced 20 g/L of 2,3-butanediol at a yield of 0.27 g 2,3-butanediol/g xylose and a production efficiency of 0.18 g/Lh.

Meanwhile, as a result of fermentation in the mixed sugar of 2% glucose and 8% xylose, BD4X exhibited an yield of 0.29 g 2,3-butanediol/g mixed sugar, higher than when only xylose was used as a substrate, and finally produced 26 g/L of 2,3-butanediol.

Figure 9:
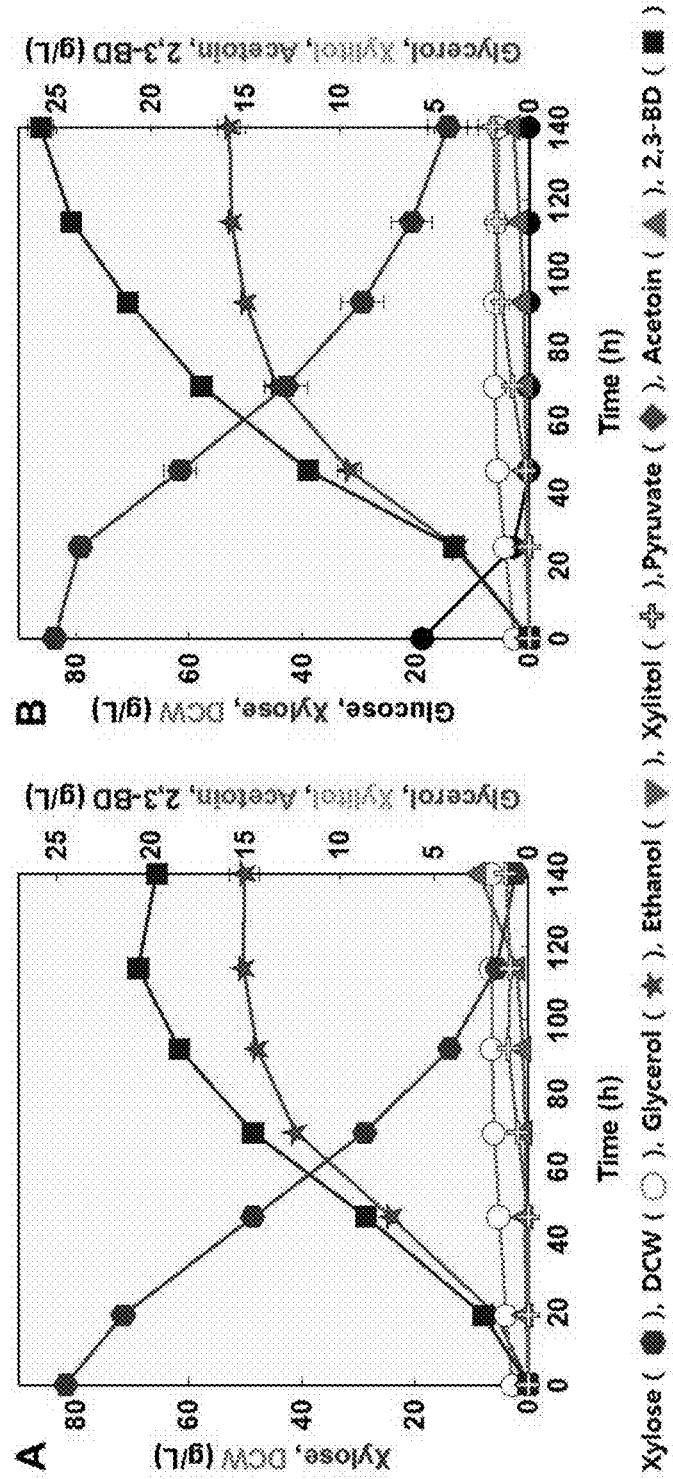
FIG. 9 shows results of production of 2,3-butanediol from high-concentration xylose, and mixed sugar of glucose and xylose under microaerobic conditions by BD4X strains. (A)

FIG. 9 shows results of production of 2,3-butanediol from high-concentration xylose, and mixed sugar of glucose and xylose under microaerobic conditions by BD4X strains. (A) YP medium containing 8% xylose, (B) YP medium containing 2% glucose and 8% xylose.

Example 10

Analysis of 2,3-Butanediol Stereoisomers Produced by BD4X (1) Introduction 2,3-butanediol stereoisomers depend on microorganism producing 2,3-butanediol. In order to confirm the stereoisomers of 2,3-butanediol produced by BD4X, a supernatant of cell culture solution was analyzed by a gas chromatography (GC) system equipped with a chiral column.

(2) Materials and Methods 2,3-butanediol stereoisomers were analyzed using a gas chromatography (GC) system equipped with a HP-Chiral-20B GC column. Analysis conditions are as follows:

Mobile gas: inlet (30 mL/min)

Inlet temperature: 240° C., ion sensor temperature: 250° C.

Temperature control of column: start (50° C.)->elevation of temperature (10° C./min)->maintenance of temperature (80° C. for 5 min)->elevation of temperature (5° C./min)->maintenance of temperature (100° C. for 7 min)->elevation of temperature (40° C./min)->maintenance of temperature (240° C. for 5 min)

(3) Results

In general, about of 70 to 80% of the 2,3-butanediol produced by yeast was (R,R)-2,3-butanediol and the remaining was meso-2,3-butanediol. However, 97% or more of 2,3-butanediol produced by BD4X was (R,R)-2,3-butanediol. FIG. 10 shows results of GC analysis on stereoisomers of 2,3-butanediol produced by BD4X strains, wherein (A): acetoin and 2,3-butanediol stereoisomer standards, (B): 2,3-butanediol stereoisomers produced by BD4X strains through metabolization of glucose, and (C): 2,3-butanediol stereoisomers produced by BD4X strains through metabolization of xylose.

Example 11

Fed-Batch Culture of BD4X (1) Introduction

Xylose fed-batch culture was performed to finally determine whether or not BD4X is a strain suited to produce 2,3-butanediol from xylose.

(2) Materials and Methods

Fed-batch culture was performed at an initial inoculation OD of 10 to obtain high-concentration 2,3-butanediol. A 1 L fermentor was used for fed-batch culture and the culture was performed at a pH of 5.8 and a temperature at 30° C. Strains were inoculated in 500 mL of a YP medium under microaerobic conditions (300 rpm, 0.25 vvm). Fermentation was performed by supplying glucose at a constant concentration of 1 g/L or less and intermittently adding 8% (w/v) xylose. That is, xylose was continuously supplied at a rate of 80 g/L using 800 g/L of a xylose solution when xylose was consumed at 80 g/L in an initial stage, and glucose was continuously supplied at a rate of 1.2 g/h or 0.3 g/h using 800 g/L of a glucose solution while performing fermentation.

(3) Results 43.6 g/L of 2,3-butanediol was produced for 273 hours through the glucose-restricted 8% fed-batch culture. FIG. 11 shows results of xylose fed-batch culture of BD4X strains under microaerobic conditions.

Example 12

Fed-Batch Culture (Glucose, Xylose Fed-Batch Culture) of BD4X (1) Introduction

Glucose and xylose fed-batch culture was performed. Fermentation was performed by intermittently adding mixed sugar of 7% (w/v) glucose and 4% (w/v) xylose.

(2) Materials and methods

Fed-batch culture was performed at an initial inoculation OD of 10 to obtain high-concentration 2,3-butanediol. A 1 L fermentor was used for fed-batch culture and the culture was performed at a pH of 5.8 and a temperature of 30° C. Strains were inoculated in 500 mL of a YP medium under microaerobic conditions (300 rpm, 0.25 vvm). Fermentation was performed by supplying glucose at a constant concentration of 1 g/L or less and intermittently adding mixed sugar of 7% glucose and 4% xylose. The mixed sugar was intermittently added at 7% of glucose and 4% of xylose using 800 g/L of a solution of glucose and xylose when 70 g/L of glucose and 40 g/L of xylose were completely consumed.

(3) Results 52.2 g/L of 2,3-butanediol was produced for 290 hours through fed-batch culture using the mixed sugar. In this case, the yield was 0.26 g 2,3-butanediol/g mixed sugar. FIG. 12 shows results of glucose and xylose fed-batch culture of BD4X strains under microaerobic conditions. Conventional yeasts produce a small amount of 2,3-butanediol, but it is demonstrated that the present invention establishes recombinant yeasts capable of producing 2,3-butanediol at a high level and enables production of 2,3-butanediol at high production efficiency through optimization of fermentation processes.

In addition, the present invention also establishes a system using lignocellulose-derived xylose as a substrate in order to improve economic efficiency of 2,3-butanediol production and enables production of 2,3-butanediol at high production efficiency from xylose.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A recombinant *Saccharomyces cerevisiae* strain comprising genetic modifications such that functions of pyruvate decarboxylase are lost and an MTHI gene is modified such that the resultant MthI protein comprises a proline in place of an alanine at the 81$^{st}$ amino acid as set forth in SEQ ID NO: 17, and acetolactate synthase, acetolactate decarboxylase and butanediol dehydrogenase are expressed.

2. The recombinant *Saccharomyces cerevisiae* according to claim 1, wherein the loss of functions of the pyruvate decarboxylase is carried out by partially disrupting or entirely deleting each of a PDC1 gene encoding pyruvate decarboxylase 1 and a PDC5 gene encoding pyruvate decarboxylase 5.

3. A method of producing 2,3-butanediol comprising inoculating a medium containing glucose with the recombinant *Saccharomyces cerevisiae* according to claim 1, followed by culturing.

4. The method according to claim 3, wherein the culturing is performed while supplying oxygen.

5. The method according to claim 3, wherein the culturing is fed-batch culturing comprising continuously supplying glucose.

6. A recombinant *Saccharomyces cerevisiae* comprising genetic modifications such that xylose reductase, xylitol dehydrogenase and xylulose kinase are expressed, functions of pyruvate decarboxylase are lost, and acetolactate synthase, acetolactate decarboxylase and butanediol dehydrogenase are expressed and an MTHI gene is modified such that the resultant MthI protein comprises a proline in place of an alanine at the 81$^{st}$ amino add as set forth in SEQ ID NO: 17.

7. The recombinant *Saccharomyces cerevisiae* according to claim 6, wherein the loss of functions of the pyruvate decarboxylase is carried out by partially disrupting or entirely deleting each of a PDC1 gene encoding pyruvate decarboxylase 1 and a PDC5 gene encoding pyruvate decarboxylase 5.

8. A method of producing 2,3-butanediol comprising inoculating a medium containing xylose with the recombinant *Saccharomyces cerevisiae* according to claim 6, followed by culturing.

9. The method according to claim 8, wherein the medium further contains glucose.

10. The method according to claim 8, wherein the culturing is performed while supplying oxygen.

11. The method according to claim 8, wherein the culturing is fed-batch culturing comprising continuously supplying xylose.

12. The method according to claim 9, wherein the culturing is fed-batch culturing comprising continuously supplying xylose and glucose.

* * * * *

SEQUENCE LISTING

<160> NUMBER OF SEQ ID NOS: 17

<210> SEQ ID NO 1
<211> LENGTH: 28
<212> TYPE: DNA
<213> ORGANISM: Saccharomyces cerevisiae

<400> SEQUENCE: 1
gctctagact tgaaaaagga acaagctc                                          28

<210> SEQ ID NO 2
<211> LENGTH: 20
<212> TYPE: DNA
<213> ORGANISM: Saccharomyces cerevisiae

<400> SEQUENCE: 2
gatttgactg tgttattttg                                                   20

<210> SEQ ID NO 3
<211> LENGTH: 85
<212> TYPE: DNA
<213> ORGANISM: Saccharomyces cerevisiae

<400> SEQUENCE: 3
caaaataaca cagtcaaatc ggcgcgcctt tttatgtaac gaaaaataaa ttggttcata      60
ttattactga ttcggtaatc tccga                                             85

<210> SEQ ID NO 4
<211> LENGTH: 69
<212> TYPE: DNA
<213> ORGANISM: Saccharomyces cerevisiae

<400> SEQUENCE: 4
gctctagatg cttataaaac tttaactaat aattagagat taaatcgcgg gtaataactg      60
atataatta                                                               69

<210> SEQ ID NO 5
<211> LENGTH: 19
<212> TYPE: DNA
<213> ORGANISM: Saccharomyces cerevisiae

<400> SEQUENCE: 5
gactgtcggc aacttcttg                                                    19

<210> SEQ ID NO 6
<211> LENGTH: 28
<212> TYPE: DNA
<213> ORGANISM: Saccharomyces cerevisiae

<400> SEQUENCE: 6
gctctagaag gttcaaagac tctataag                                          28

<210> SEQ ID NO 7
<211> LENGTH: 21
<212> TYPE: DNA
<213> ORGANISM: Saccharomyces cerevisiae

<400> SEQUENCE: 7
gttcttcttg ttattgtatt g                                                 21

<210> SEQ ID NO 8
<211> LENGTH: 87

<212> TYPE: DNA
<213> ORGANISM: Saccharomyces cerevisiae

<400> SEQUENCE: 8
caatacaata acaagaagaa cggcgcgcct agtataataa atttctgatt tggtttaaaa    60
tatcaactag attcggtaat ctccgaa    87

<210> SEQ ID NO 9
<211> LENGTH: 69
<212> TYPE: DNA
<213> ORGANISM: Saccharomyces cerevisiae

<400> SEQUENCE: 9
gctctagact atatctatgc caattattta cctaaacatc tataacctgg gtaataactg    60
atataatta    69

<210> SEQ ID NO 10
<211> LENGTH: 19
<212> TYPE: DNA
<213> ORGANISM: Saccharomyces cerevisiae

<400> SEQUENCE: 10
aggtacaaaa ccgaatacg    19

<210> SEQ ID NO 11
<211> LENGTH: 31
<212> TYPE: DNA
<213> ORGANISM: Saccharomyces cerevisiae

<400> SEQUENCE: 11
cgggatccat gttgacaaaa gcaacaaaag a    31

<210> SEQ ID NO 12
<211> LENGTH: 29
<212> TYPE: DNA
<213> ORGANISM: Saccharomyces cerevisiae

<400> SEQUENCE: 12
ccgctcgagc tagagagctt tcgttttca    29

<210> SEQ ID NO 13
<211> LENGTH: 29
<212> TYPE: DNA
<213> ORGANISM: Saccharomyces cerevisiae

<400> SEQUENCE: 13
ccgctcgagt tattcagggc ttccttcag    29

<210> SEQ ID NO 14
<211> LENGTH: 32
<212> TYPE: DNA
<213> ORGANISM: Saccharomyces cerevisiae

<400> SEQUENCE: 14
cgggatccaa aatgagagct ttggcatatt tc    32

<210> SEQ ID NO 15
<211> LENGTH: 31
<212> TYPE: DNA
<213> ORGANISM: Saccharomyces cerevisiae

<400> SEQUENCE: 15
ccgctcgagt tacttcattt caccgtgatt g                                    31

<210> SEQ ID NO 16
<211> LENGTH: 433
<212> TYPE: PRT
<213> ORGANISM: Saccharomyces cerevisiae

<400> SEQUENCE: 16

Met Phe Val Ser Pro Pro Ala Thr Ser Lys Asn Gln Val Leu Gln
1               5                   10                  15

Arg Arg Pro Leu Glu Ser Thr Asn Ser Asn His Gly Phe Ala Ser Ser
            20                  25                  30

Leu Gln Ala Ile Pro Glu Asn Thr Met Ser Gly Ser Asp Asn Ala Ser
        35                  40                  45

Phe Gln Ser Leu Pro Leu Ser Met Ser Ser Gln Ser Thr Thr Ser
    50                  55                  60

Ser Arg Arg Glu Asn Phe Val Asn Ala Pro Glu Tyr Thr Asp Arg
65                  70                  75                  80

Ala Arg Asp Glu Ile Lys Lys Arg Leu Leu Ala Ser Ser Pro Ser Arg
                85                  90                  95

Arg Ser His His Ser Ser Ser Met His Ser Ala Ser Arg Ser Ser
            100                 105                 110

Val Ala Glu Ser Gly Ser Leu Leu Ser Asp Asn Ala Ser Ser Tyr Gln
            115                 120                 125

Ser Ser Ile Phe Ser Ala Pro Ser Thr Val His Thr Gln Leu Thr Asn
        130                 135                 140

Asp Ser Ser Phe Ser Glu Phe Pro Asn His Lys Leu Ile Thr Arg Val
145                 150                 155                 160

Ser Leu Asp Glu Ala Leu Pro Lys Thr Phe Tyr Asp Met Tyr Ser Pro
                165                 170                 175

Asp Ile Leu Leu Ala Asp Pro Ser Asn Ile Leu Cys Asn Gly Arg Pro
            180                 185                 190

Lys Phe Thr Lys Arg Glu Leu Leu Asp Trp Asp Leu Asn Asp Ile Arg
        195                 200                 205

Ser Leu Leu Ile Val Glu Lys Leu Arg Pro Glu Trp Gly Asn Gln Leu
210                 215                 220

Pro Glu Val Ile Thr Val Gly Asp Asn Met Pro Gln Phe Arg Leu Gln
225                 230                 235                 240

Leu Leu Pro Leu Tyr Ser Ser Asp Glu Thr Ile Ile Ala Thr Leu Val
                245                 250                 255

His Ser Asp Leu Tyr Met Glu Ala Asn Leu Asp Tyr Glu Phe Lys Leu
            260                 265                 270

Thr Ser Ala Lys Tyr Thr Val Ala Thr Ala Arg Lys Arg His Glu His
        275                 280                 285

Ile Thr Gly Arg Asn Glu Ala Val Met Asn Leu Ser Lys Pro Glu Trp
    290                 295                 300

Arg Asn Ile Ile Glu Asn Tyr Leu Leu Asn Ile Ala Val Glu Ala Gln
305                 310                 315                 320

Cys Arg Phe Asp Phe Lys Gln Arg Cys Ser Glu Tyr Lys Lys Trp Lys
                325                 330                 335

Leu Gln Gln Ser Asn Leu Lys Arg Pro Asp Met Pro Pro Ser Ile
            340                 345                 350

Ile Pro Arg Lys Asn Ser Thr Glu Thr Lys Ser Leu Leu Lys Lys Ala
        355                 360                 365

```
Leu Leu Lys Asn Ile Gln Leu Lys Asn Pro Asn Asn Asn Leu Asp Glu
        370                 375                 380
Leu Met Met Arg Ser Ser Ala Ala Thr Asn Gln Gln Gly Lys Asn Lys
385                 390                 395                 400
Val Ser Leu Ser Lys Glu Glu Lys Ala Thr Ile Trp Ser Gln Cys Gln
                405                 410                 415
Ala Gln Val Tyr Gln Arg Leu Gly Leu Asp Trp Gln Pro Asp Ser Val
                420                 425                 430
Ser

<210> SEQ ID NO 17
<211> LENGTH: 433
<212> TYPE: PRT
<213> ORGANISM: Saccharomyces cerevisiae

<400> SEQUENCE: 17

Met Phe Val Ser Pro Pro Ala Thr Ser Lys Asn Gln Val Leu Gln
1                5                  10                  15
Arg Arg Pro Leu Glu Ser Thr Asn Ser Asn His Gly Phe Ala Ser Ser
                20                  25                  30
Leu Gln Ala Ile Pro Glu Asn Thr Met Ser Gly Ser Asp Asn Ala Ser
            35                  40                  45
Phe Gln Ser Leu Pro Leu Ser Met Ser Ser Gln Ser Thr Thr Ser
50                  55                  60
Ser Arg Arg Glu Asn Phe Val Asn Ala Pro Pro Glu Tyr Thr Asp Arg
65                  70                  75                  80
Pro Arg Asp Glu Ile Lys Lys Arg Leu Leu Ala Ser Ser Pro Ser Arg
                85                  90                  95
Arg Ser His His Ser Ser Ser Met His Ser Ala Ser Arg Arg Ser Ser
                100                 105                 110
Val Ala Glu Ser Gly Ser Leu Leu Ser Asp Asn Ala Ser Ser Tyr Gln
            115                 120                 125
Ser Ser Ile Phe Ser Ala Pro Ser Thr Val His Thr Gln Leu Thr Asn
130                 135                 140
Asp Ser Ser Phe Ser Glu Phe Pro Asn His Lys Leu Ile Thr Arg Val
145                 150                 155                 160
Ser Leu Asp Glu Ala Leu Pro Lys Thr Phe Tyr Asp Met Tyr Ser Pro
                165                 170                 175
Asp Ile Leu Leu Ala Asp Pro Ser Asn Ile Leu Cys Asn Gly Arg Pro
            180                 185                 190
Lys Phe Thr Lys Arg Glu Leu Leu Asp Trp Asp Leu Asn Asp Ile Arg
            195                 200                 205
Ser Leu Leu Ile Val Glu Lys Leu Arg Pro Glu Trp Gly Asn Gln Leu
210                 215                 220
Pro Glu Val Ile Thr Val Gly Asp Asn Met Pro Gln Phe Arg Leu Gln
225                 230                 235                 240
Leu Leu Pro Leu Tyr Ser Ser Asp Glu Thr Ile Ile Ala Thr Leu Val
                245                 250                 255
His Ser Asp Leu Tyr Met Glu Ala Asn Leu Asp Tyr Glu Phe Lys Leu
            260                 265                 270
Thr Ser Ala Lys Tyr Thr Val Ala Thr Ala Arg Lys Arg His Glu His
            275                 280                 285
Ile Thr Gly Arg Asn Glu Ala Val Met Asn Leu Ser Lys Pro Glu Trp
            290                 295                 300
```

-continued

```
Arg Asn Ile Ile Glu Asn Tyr Leu Leu Asn Ile Ala Val Glu Ala Gln
305             310             315             320

Cys Arg Phe Asp Phe Lys Gln Arg Cys Ser Glu Tyr Lys Lys Trp Lys
            325             330             335

Leu Gln Gln Ser Asn Leu Lys Arg Pro Asp Met Pro Pro Ser Ile
        340             345             350

Ile Pro Arg Lys Asn Ser Thr Glu Thr Lys Ser Leu Leu Lys Lys Ala
        355             360             365

Leu Leu Lys Asn Ile Gln Leu Lys Asn Pro Asn Asn Asn Leu Asp Glu
        370             375             380

Leu Met Met Arg Ser Ser Ala Ala Thr Asn Gln Gln Gly Lys Asn Lys
385             390             395             400

Val Ser Leu Ser Lys Glu Glu Lys Ala Thr Ile Trp Ser Gln Cys Gln
            405             410             415

Ala Gln Val Tyr Gln Arg Leu Gly Leu Asp Trp Gln Pro Asp Ser Val
            420             425             430

Ser
```